(12) United States Patent
Niznick

(10) Patent No.: US 7,396,231 B2
(45) Date of Patent: Jul. 8, 2008

(54) FLARED IMPLANT EXTENDER FOR ENDOSSEOUS DENTAL IMPLANTS

(76) Inventor: Gerald A. Niznick, 3993 Howard Hughes Pkwy., #540, Las Vegas, NV (US) 89109

( * ) Notice: Subject to any disclaimer, the term of this patent is extended or adjusted under 35 U.S.C. 154(b) by 248 days.

(21) Appl. No.: 11/074,048

(22) Filed: Mar. 7, 2005

(65) Prior Publication Data

US 2006/0199149 A1 Sep. 7, 2006

(51) Int. Cl.
*A61C 8/00* (2006.01)
(52) U.S. Cl. .................. 433/173; 433/172; 433/174
(58) Field of Classification Search ........... 433/173, 433/174, 172
See application file for complete search history.

(56) References Cited

U.S. PATENT DOCUMENTS

| | | | | | |
|---|---|---|---|---|---|
| 4,872,839 | A | * | 10/1989 | Brajnovic | 433/173 |
| 5,286,195 | A | * | 2/1994 | Clostermann | 433/172 |
| 5,873,722 | A | * | 2/1999 | Lazzara et al. | 433/173 |
| 5,989,028 | A | * | 11/1999 | Niznick | 433/173 |
| 6,012,923 | A | * | 1/2000 | Bassett et al. | 433/172 |
| 6,287,117 | B1 | * | 9/2001 | Niznick | 433/173 |

\* cited by examiner

*Primary Examiner*—Cris L. Rodriguez
*Assistant Examiner*—Hao D Mai
(74) *Attorney, Agent, or Firm*—Patrick F. Bright

(57) ABSTRACT

An endosseous dental implants include a flared implant extender with an internal passage and with an unthreaded external surface that tapers downwardly from the proximal end of the extender toward its distal end that has a size and shape appropriate to cover the top surface of the implant.

4 Claims, 3 Drawing Sheets

FLARED IMPLANT EXTENDER FOR ENDOSSEOUS DENTAL IMPLANTS

This invention relates to root-form two-part endosseous dental implants for insertion into an opening in the jawbone of a patient that include a healing screw and an optional implant extender.

Such two-part implants include an implant with an unthreaded neck portion that, in a shorter version, meaning a neck length in the range of about 1 mm to about 2 mm, can place the top surface level with the crest of the bone, and in a longer version, meaning a neck length in the range of about 2 mm to about 5 mm, can place the top surface so that it extends above the top surface of the crest of the bone tissue. Due to variations in tissue thickness, the longer version neck may require an extender to penetrate above the gum tissue. The shorter version neck almost always needs an extender to penetrate above the gum tissue. The implant has an opening at the top to an internally-threaded shaft extending into, and ending inside the implant.

An optional flared implant extender, preferably about 2 to about 3 mm in length, fits on, and covers the top surface of the implant. A healing screw with a threaded shank of sufficient length passes through a longitudinal passage inside the implant extender, and engages the internally-threaded shaft inside the implant. These extenders include a top portion that flares outwardly from the proximal ends of the implants. The healing screw may also sit on, and cover the top of the implant without the implant extender, thus covering the opening to the internal shaft.

Some embodiments of these extenders may include, in the top portion, a groove or recess of a size and shape complementary to the head portion of the healing screw. In these embodiments, the head portion of the healing screw, when the healing screw is placed into the longitudinal passage inside the implant extender, may lie in substantially the same plane as the top surface of the extender, or may protrude above this plane.

Two-part dental implants include an implant and a separate abutment, and may be placed with a two-stage surgical protocol, where, for example, a dental implant with a short neck is placed level with the crest of a patient's jawbone, the top surface is seated with a cover screw, and the soft tissue is sutured over the top of the cover screw. The first stage comprises inserting an implant, such as the ZIMMER'S SCREW-VENT.®, NOBEL BIO-CARE'S BRANEMARK®, and REPLACE SELECT implants, into the jaw bone, and burying it beneath the mucosal gum tissue for a submerged healing period. See, generally, U.S. Pat. No. 4,960,381, whose contents are incorporated herein by reference as though fully set forth here. Such implants include an externally-threaded or unthreaded, tapered or untapered body portion, and an internally-threaded shaft. The internally-threaded region is of sufficient length to accommodate an optional implant extender, and a healing screw with a threaded shank of sufficient length to pass through a longitudinal passage inside the extender, and to engage the internal threads of the implant, with internally threaded region and threaded shaft of the healing screw also being of sufficient length to allow full seating of the head of the healing screw on the top surface of the implant, in the absence of the use of the implant extender.

The second stage comprises exposing the top of the submerged implant to allow attachment of an abutment. The abutment has a portion that extends above the gum tissue to allow attachment of a prosthesis. Submerged body implants and even non-submerged implants with a body and neck are usually two-part implants, requiring attachment to the implant of a separate abutment to support a prosthesis.

Short-necked implants, and implants with longer necks, may be placed in an opening of the jawbone of a patient, in a one-stage surgical protocol. An extender or healing collar is placed atop such short-neck implants; an extender, or cover screw, is placed atop such long-neck implants. The resulting assembly will extend through the mucosal tissue and maintain the tissue opening. This one-stage surgical protocol eliminates cutting the soft tissue and exposing the top of the implant to remove a cover screw and to attach an abutment to the top surface of the implant, which would be the second stage of a two-stage surgical protocol. Examples of two-part implants designed for a one-stage surgical protocol are Straumann's ITI implant and Zimmer's Swiss-Plus implant.

Many two-part implants include, at the top, a wrench-engaging surface, such as an internal or external hex or spline, or internal multi-sided, multi-lobed surfaces. Such wrench-engaging surfaces may be used for insertion of threaded implants into an opening in a patient's jawbone, or for connection of a multi-part, screw-retained abutments that engage the wrench-engaging surface to provide anti-rotational stability to the abutment. Such a connection provides a stable base for attachment of a cemented single tooth restoration. All of these implants include an internally-threaded shaft extending downwardly from the top of the implant, and terminating inside the implant. This shaft is of sufficient length, and includes a threaded region of sufficient length, to engage the threaded distal end of the healing screw, with or without the flared extender atop the implant. The overall length of these implants is, preferably, at least about 8 mm, with the internally threaded shaft region of the internal shaft preferably at least about 4-5 mm in length, to accommodate the healing screw, with or without the implant extender.

BRIEF DESCRIPTION OF THE DRAWINGS

The invention can better be understood by reference to the drawings in which.

DETAILED DESCRIPTION OF THE DRAWINGS

Figure 1:
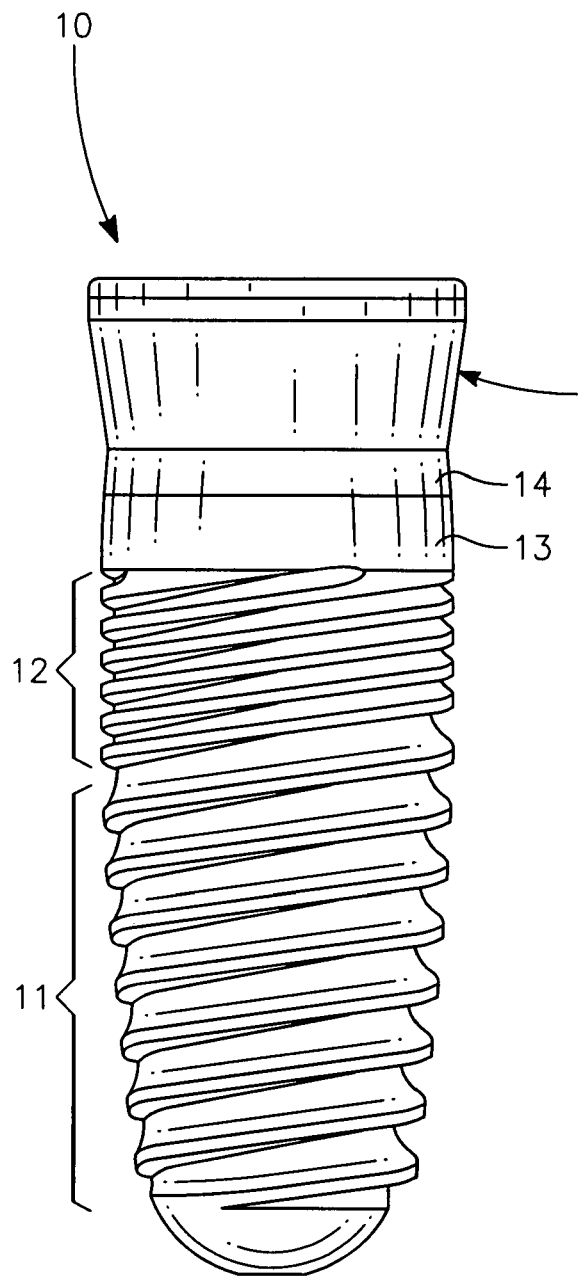
FIG. 1 is a side elevation view of an externally-threaded, tapered, endosseous dental implant, having an outwardly flaring implant extender secured thereto by a fixation or healing screw.

FIGS. 1-6 show externally-threaded, tapered endosseous dental implant 10. Implant 10 includes a distal, externally-threaded region 11 and a proximal externally-threaded region 12. The threads in region 12 have the same pitch as the threads in externally-threaded region 11. The spacing of the threads in region 12 is approximately half that of the spacing in region 11. Endosseous dental implant 10 also includes, proximal to the externally-threaded region 12, unthreaded cylindrical portion 13, and tapering proximal region 14.

Figure 2:
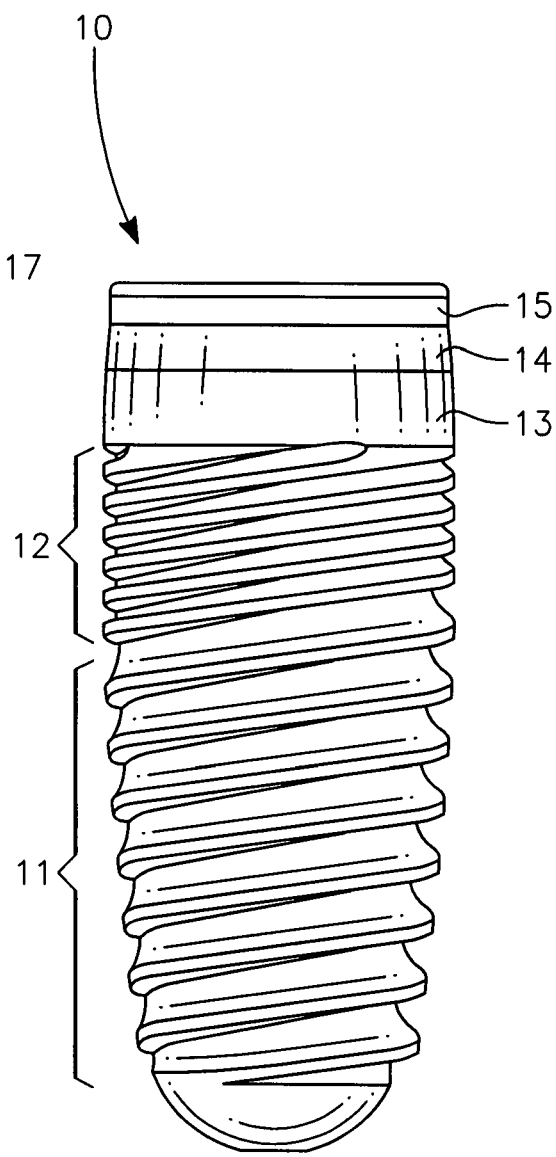
FIG. 2 is a side elevation view of the endosseous dental implant shown in FIG. 1, without the extender shown in FIG. 1, but with the fixation screw secured inside the endosseous dental implant.
Figures 3, 4:
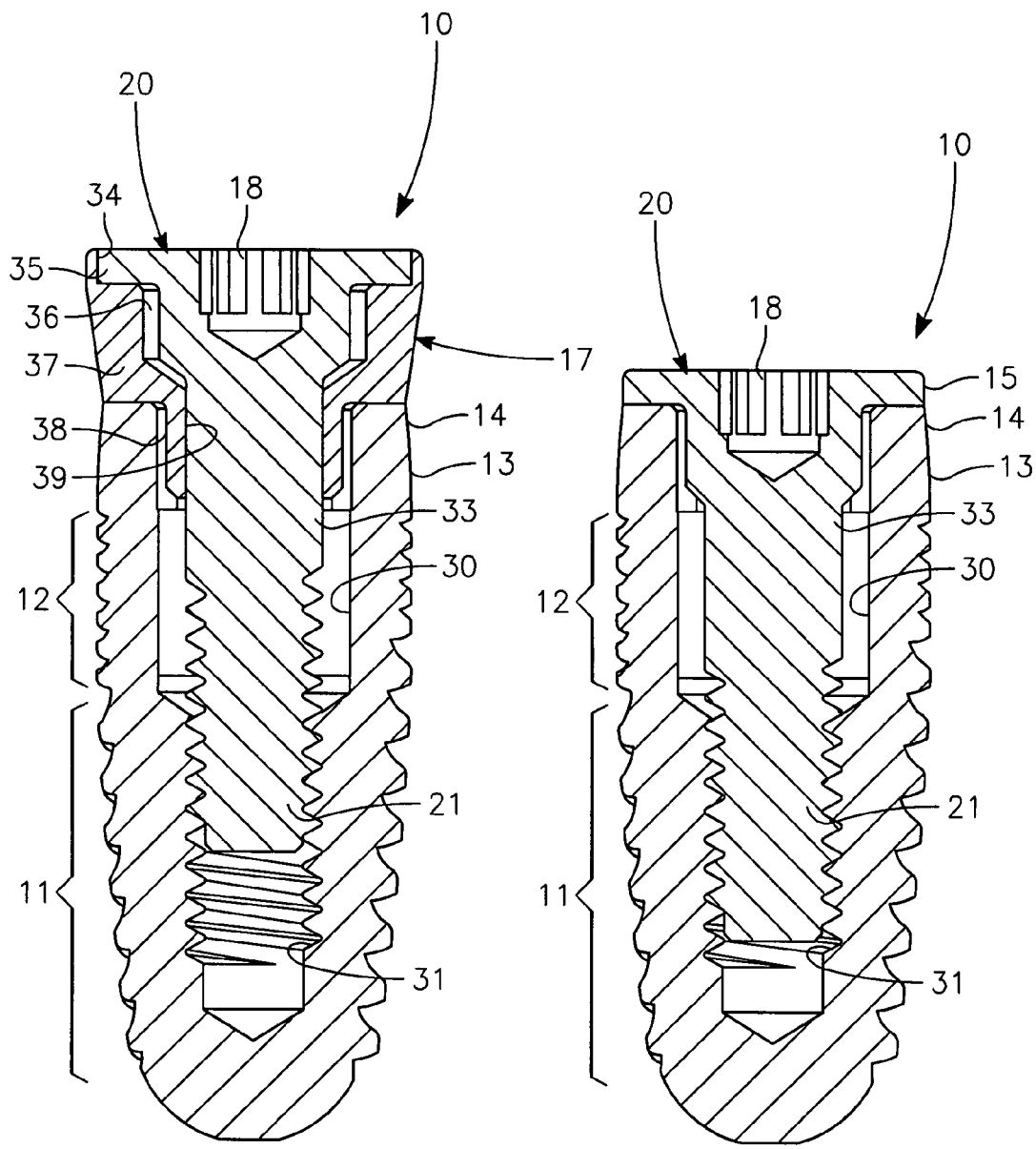
FIG. 3 is a side elevation view, in vertical cross-section, of the endosseous dental implant/fixation screw assembly shown in FIG. 2, showing that the externally-threaded shank of the fixation screw engages the threads of the internal passage in the implant.
FIG. 4 is a side elevation view, in vertical cross-section, of the endosseous dental implant/flared implant extender/fixation screw combination shown in FIG. 1, showing in detail how the fixation screw holds the flared implant extender in place atop the implant by engagment of the externally-threaded shank of the fixation screw with the internal threads of the implant.
Figures 5, 6:
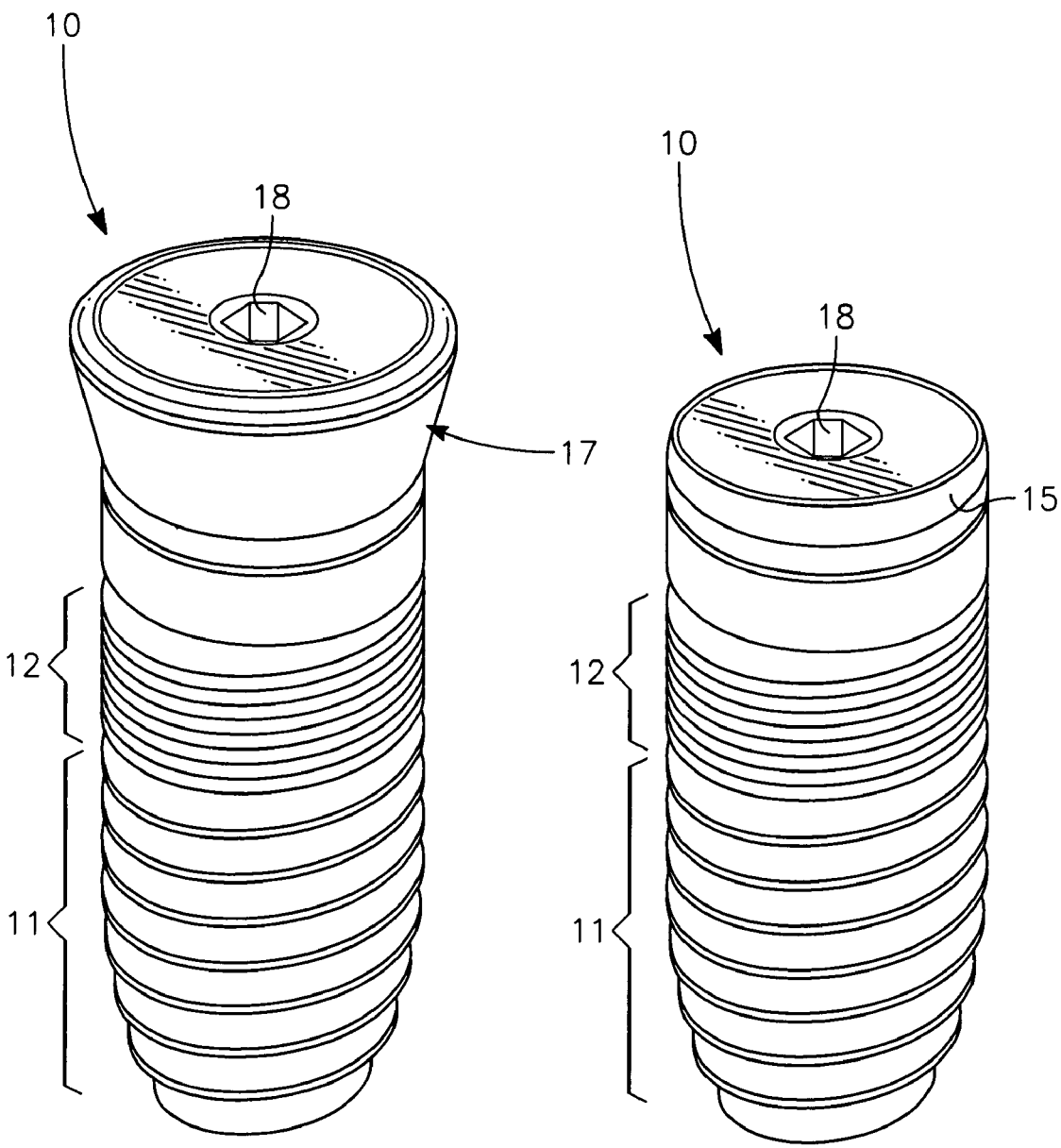
FIG. 5 is a perspective view of the endosseous dental implant/implant extender/fixation screw assembly shown in FIGS. 1 and 4.
FIG. 6 is a perspective view of the endosseous dental implant/fixation screw assembly shown in FIGS. 2 and 3.

As FIGS. 2, 3 and 6 show, fixation screw 20 fits into internal passage 30 inside implant 10. Passage 30 includes threaded region 31 and unthreaded region 32. Fixation screw 20 includes head portion 15 and threaded distal shank 21. Upon insertion of fixation screw 20 into passage 30, the threads on shank 21 engage threaded region 31, holding fixation screw 20 in place inside implant 10.

Fixation screw 20 includes a proximal opening into multi-sided passage 18 for insertion of a tool of complementary size and shape, to insert, twist, turn and/or hold fixation screw 20. Screw 20 also includes unthreaded middle portion 33; proximal thereto, cylindrical portion 34; and, atop portion 34, circumferential shoulder or flange 35.

FIGS. 1, 4 and 5 show fixation screw 20 threaded into internal passage 30, holding in place, atop implant 10, inwardly flaring, distally-extending implant extender 17. Extender 17 includes proximal countersunk region 34, which has a size and shape appropriate to receive and engage flange 35 atop fixation screw 20. Implant extender 17 also includes flat, circumferentially-extending shoulder 35, and longitudinal through passage 36. The body of extender 17 includes outwardly flaring proximal portion 37, flat surface 38 distal to surface 37, and passage 39 distal to portion 37.

What is claimed is:

1. An endosseous, root-form dental implant for insertion through an opening in the mucosal tissue and into an opening in the jawbone of a patient includes a body portion having a top surface that includes a proximal opening; an internally-threaded shaft extending into said implant, from said top surface; a healing screw comprising a head portion with an undersurface joined to a shank portion having a threaded distal end portion, said head portion having a size and shape sufficient to cover a proximal opening into said internally-threaded shaft; and a flared implant extender that is of sufficient length to extend through the opening in the mucosal tissue atop the opening in the jawbone of a patient, and that is of sufficient size and shape to maintain the opening in said mucosal tissue, said extender having a proximal end and a distal end, and having an unthreaded external surface that tapers continuously inwardly from the proximal end to the distal end of said extender, said extender having a distal end portion of a size and shape sufficient to cover the top surface of said implant, said extender including an internal longitudinal passage of sufficient size and shape to permit the threaded distal end portion of said healing screw to pass through said internal longitudinal passage, said internal longitudinal passage including a proximal opening, the head portion of said healing screw having a size and shape sufficient to cover said proximal opening of the internal longitudinal passage; said internally-threaded shaft of said implant, having a threaded region sufficiently long to engage said threaded distal end portion of said healing screw with said implant extender in place atop said implant and with the undersurface of the head portion of said healing screw covering said proximal opening of the internal longitudinal passage or, if said extender is absent, covering the opening into said internally-threaded shaft of said implant.

2. The dental implant of claim 1 wherein the head portion of said healing screw is of size and shape sufficient to cover the top surface of said implant.

3. The dental implant of claim 1 or claim 2 wherein said extender includes, in its top surface, a groove or recess of a size and shape appropriate to receive the head portion of said healing screw.

4. The dental implant of claim 3 wherein said head portion lies in substantially the same plane as the top surface of said extender when said healing screw is inserted into said internal longitudinal passage of said extender.

* * * * *